United States Patent
Donskoy et al.

(10) Patent No.: US 6,301,967 B1
(45) Date of Patent: Oct. 16, 2001

(54) METHOD AND APPARATUS FOR ACOUSTIC DETECTION AND LOCATION OF DEFECTS IN STRUCTURES OR ICE ON STRUCTURES

(75) Inventors: Dimitri M. Donskoy; Alexander M. Sutin, both of Hoboken, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 09/239,133

(22) Filed: Jan. 28, 1999

Related U.S. Application Data

(60) Provisional application No. 60/073,567, filed on Feb. 3, 1998.

(51) Int. Cl.[7] .......................... G01N 29/00; G01H 13/00
(52) U.S. Cl. .................. 73/579; 73/597; 73/602
(58) Field of Search .............................. 73/579, 583, 584, 73/587, 590, 591, 592, 596, 597, 598, 599, 602; 244/134 R, 134 F

(56) References Cited

U.S. PATENT DOCUMENTS

| | | | |
|---|---|---|---|
| 3,705,381 | * 12/1972 | Pipkin ............................. 340/3 R |
| 3,898,840 | 8/1975 | McElroy ............................. 73/67.9 |
| 4,233,843 | * 11/1980 | Thompson et al. ............... 73/579 |
| 4,281,547 | * 8/1981 | Hinshaw et al. ................. 73/579 |
| 4,381,674 | * 5/1983 | Abts .................................. 73/599 |
| 4,461,178 | 7/1984 | Chamuel ............................ 73/599 |
| 4,502,329 | * 3/1985 | Fukunaga et al. ................ 73/573 |
| 4,611,492 | 9/1986 | Koosmann ......................... 73/579 |
| 4,689,993 | 9/1987 | Slettemoen ........................ 73/579 |
| 4,944,185 | 7/1990 | Clark, Jr. et al. ................. 73/579 |
| 5,024,090 | * 6/1991 | Pettigrew et al. ................ 73/572 |
| 5,144,838 | 9/1992 | Tsuboi ............................. 73/579 |
| 5,170,666 | 12/1992 | Larsen ............................. 73/571 |
| 5,179,860 | 1/1993 | Tsuboi ............................. 73/579 |
| 5,206,806 | 4/1993 | Gerardi et al. .............. 364/424.06 |
| 5,214,960 | 6/1993 | Tsuboi ............................. 73/579 |
| 5,284,058 | 2/1994 | Jones ............................. 73/579 |
| 5,355,731 | 10/1994 | Dixon et al. ..................... 73/579 |
| 5,425,272 | 6/1995 | Rhodes et al. ................... 73/579 |
| 5,456,114 | 10/1995 | Liu et al. ......................... 73/597 |
| 5,520,052 | 5/1996 | Perchersky ....................... 73/579 |
| 5,528,924 | 6/1996 | Wajid et al. .................... 73/24.06 |
| 5,557,969 | * 9/1996 | Jordan ............................ 73/592 |
| 5,621,400 | 4/1997 | Corbi ............................. 340/962 |
| 5,650,610 | 7/1997 | Gagnon .......................... 250/225 |
| 5,736,642 | 4/1998 | Yost et al. ...................... 73/602 |
| 5,748,091 | 5/1998 | Kim ............................. 340/583 |
| 5,823,474 | 10/1998 | Nunnally ........................ 244/134 |

* cited by examiner

Primary Examiner—Helen Kwok
(74) Attorney, Agent, or Firm—Wolff & Samson

(57) ABSTRACT

The invention relates to a method and apparatus for nondestructive testing and evaluation of materials and mechanical structures to determine their integrity reducing contact-type flaws such as cracks, fractures, delamination, unbondings, etc. and also presence of ice on a structure. The invention employs an ultrasonic probing signal and a low frequency vibration applied to a structure tested. In a structure without flaws or ice, these signals propagate independently without any interaction. If the structure contains a defect or ice thereon, the vibration varies the contact area of the defect or ice/structure interface, modulating the phase and amplitude of the higher frequency ultrasonic probing signal passing through the structure. In the frequency domain the result of this modulation manifests itself as sideband spectral components with respect to frequency of the probe wave. This can be considered as a new signal generated by a defect, so that the defect can be detected more easily when such a signal is observed. There are three modes of detection including, vibro-modulation, impact-modulation and self-modulation. The location of defects can be determined in two modes. In a first mode defect is located by moving the low frequency signal about the structure and triggering the high frequency signal immediately after the low frequency signal. Defects can be located in a second mode with a sequence of short burst high frequency signal and a signal-processing algorithm which selects the sequences reflected from various areas of the tested structure. A defect can be quantitatively analyzed by sweeping the high frequency signal over a defined frequency range and measuring, averaging and normalizing the amplitudes of the side bands.

39 Claims, 10 Drawing Sheets

FREQ 330.97 kHz

FREQ 330.97 kHz

METHOD AND APPARATUS FOR ACOUSTIC DETECTION AND LOCATION OF DEFECTS IN STRUCTURES OR ICE ON STRUCTURES

CROSS-REFERENCE TO RELATED APPLICATION

This Application claims the benefit of provisional application No. 60/073,567, filed Feb. 3, 1998.

BACKGROUND OF THE INVENTION

1. Field of the Invention

The present invention relates to a method and apparatus for acoustic detection and location of defects in structures and/or ice on structures, and more particularly, to the non-destructive acoustic testing and evaluation of materials and mechanical structures utilizing an ultrasonic probing signal and low frequency vibration signal to identify and locate ice or integrity-reducing flaws such as cracks, fractures, delamination, unbonding, etc.

2. Related Art

Conventional active acoustic methods of ice detection and of non-destructive testing (NDT) are based on the principles of linear acoustics. These include effects of reflection, scattering, transmission, and absorption of probe acoustic energy. The presence of ice or a defect leads to phase and/or amplitude variation of received signals while the frequencies of the received signals are the same as the emitted probe signals.

The principal difference between the modulation technique of the present invention and linear acoustic NDT techniques is that the modulation technique correlates the presence and characteristics of a defect or of a material such as ice, with acoustic signals whose frequencies differ from the frequencies of the emitted probe signals. These signals with different frequencies are an outcome of a modulation transformation of the probe acoustic energy by a defect.

The modulation NDT methods have a number of advantages as compared with the linear acoustic techniques. Among them are high sensitivity and applicability to highly non-homogeneous and/or geometrically complex structures, such as composites, engine components, etc.

Previous efforts at NDT techniques include:

Perchersky, U.S. Pat. No. 5,520,052, discloses a method and apparatus for determining material structural integrity by combining laser vibrometry with damping analysis techniques to determine the damping loss factor of a material. The method comprises the steps of vibrating an area to be tested over a known frequency range and measuring vibrational force and velocity as a function of time over the known frequency range. Using known vibrational analysis, a plot of the drive point mobility of the material over the pre-selected frequency range is generated from the vibrational force and velocity measurements. Once computed, the damping loss factor can be compared with a reference stamping loss factor to evaluate the structural integrity of the material.

Larsen, U.S. Pat. No. 5,170,666 discloses a nondestructive evaluation of composite materials using acoustic emissions stimulated by absorbed microwave/radiofrequency energy. A specimen is exposed to pulsed radio frequency energy to produce an elastic wave that propagates on the surface of the specimen. The wave is detected by a piezoelectric or electro-optic displacement mode transducer which produces a signal corresponding to the wave. The signal is analyzed by a processor and classified.

Tsuboi, U.S. Pat. No. 5,214,960 discloses a method and apparatus for detecting defects in an object by vibrating the object in a plurality of positions. While the test object is vibrating, signals indicative of the vibration of the test object are detected and a signal indicative of a natural vibration of the test object is produced, and a signal indicative of a defect-induced vibration of the test object is produced. The signal indicative of the natural vibration and the signal indicative of the defect-induced vibration are compared to determine whether there is a defect in the test object.

Wajid, et al., U.S. Pat. No. 5,528,924 discloses an acoustic tool for analysis of a gaseous substance, specifically a refrigerant gas, to determine whether the sample contains significant contaminants. The refrigerant is tested by introducing a vapor sample into a resonant chamber which is formed to produced two distinct resonances, the resonator having first and second necks connecting first and second volumes. A frequency generator produces a sweep of frequencies in a band and then includes the two resonances and the sweep is applied to a transducer in one of the volumes. Another transducer responsive to vibrations produces an output signal that varies in response to the amplitude of the vibrations in the chamber. A digital circuit responsive to the frequency generator and the second transducer output determines the center frequencies for the first and second resonances and determines the frequency width of these resonances to determine quality or sharpness factors for the two resonances. Then the center frequencies and sharpness factors are compared with storage data and a determination as to the nature and extent of contaminants is made.

Rhodes, et al., U.S. Pat. No. 5,425,272 discloses the use of relative resonant frequency shifts to detect cracks. At least two prominent resonant frequencies of an object are sensed and the frequency difference is measured. The ratio of the frequency difference to one of the prominent resonant frequencies is determined and compared to predetermined criteria. Resonant frequency dependent upon dimensions will shift very little while resonant frequency dependent upon stiffness will shift a relatively large amount when an object has a crack.

Dixon, et al., U.S. Pat. No. 5,355,731 discloses a method for grading production quantities of spherical objects. A resonant ultrasound spectroscopy (RUS) spectrum is generated from a spherical object. Sphere parameter values for the spherical object are determined from first components of the RUS spectrum. An asphericity value of the spherical object is determined from second components of the RUS spectrum and the spherical parameter values. The asphericity value is then compared with predetermined values to grade the spherical product.

Jones, U.S. Pat. No. 5,284,058 discloses a method for measuring complex shear or Young's modulus of a polymeric material wherein first and second beams of preselected lengths and different thickness are disposed in parallel spaced relationship firmly held at the ends thereof and first and second spaced gripping members are attached along the beams, a specimen of polymeric material is disposed between confronting surfaces of the gripping members, a time varying force is applied to one beam, the time varying displacements of the beams are measured, and the modulus of the polymeric material is calculated from the measurements.

Tsuboi, U.S. Pat. No. 5,179,860 discloses a defect detecting method which includes the steps of vibrating the object, picking up the vibration, and detecting that a spectrum of the characteristic vibration of the object to be measured is separated into two portions. The method can also be used to detect cracks by vibrating an object, picking up the vibration, and detecting that an odd order spectrum of the characteristic vibration of the object to be measured is separated into two portions. A non-through defect can be determined in the same way by detecting that an even order spectrum of the characteristic vibration of the object to be measured is separated into two portions.

Tsuboi, U.S. Pat. No. 5,144,838 discloses a defect detecting method which includes the steps of vibrating the object, picking up the vibration, and detecting that a spectrum of the characteristic vibration of the object to be measured is separated into two portions. The method can also be used to detect cracks by vibrating an object, picking up the vibration, and detecting that an odd order spectrum of the characteristic vibration of the object to be measured is separated into two portions. A non-through defect can be determined in the same way by detecting that an even order spectrum of the characteristic vibration of the object to be measured is separated into two portions.

Clark, Jr. et al., U.S. Pat. No. 4,944,185 discloses a method for nondestructively inspecting the integrity of a material by tagging the material, applying the material, activating the tagged particles to cause an inherent structural resonance in the tagged material, monitoring and measuring the structural resonance of the material with a probe, and relating the structure resonance of the material to the structural integrity of the material. The invention has particular application to a material such as an adhesive material.

Slettemoen, U.S. Pat. No. 4,689,993 discloses a method and apparatus for measuring and mapping vibrations wherein one or more local sensors and a measuring means make local registrations and frequency decompositions of the vibrations of an oscillating object. The same sensors and measuring means can also be used with an image-forming unit and an associated measuring means for local and image-forming recording of the vibrations of an oscillating object.

Chamuel, U.S. Pat. No. 4,461,178 discloses a method for ice detection wherein a flexural wave and a compressional wave is propagated through a structure. Ice impacts the propagation speed of the flexural wave, as do others, i.e. temperature, etc. These other factors are taken into account by the use of the compressional wave which provides a baseline for the structure at the particular conditions encountered.

Yost, U.S. Pat. No. 5,736,642 disclose a method of nonlinear ultrasonic scanning to detect material defects wherein first and second frequencies are propogated and combination frequencies result, i.e. a sum wave or a difference wave ($f_1 \pm f_2$).

Additionally, there have been previous efforts at producing methods for detection of ice.

Conventional methods of ice detection utilize various types of energy: cross-polarized coherent light (U.S. Pat. No. 5,650,610) laser beam (U.S. Pat. No. 5,823,474), fiber optic sensors (U.S. Pat. No. 5,748,091), electrical conductivity sensors (U.S. Pat. No. 5,621,400), piezoelectric film sensor (U.S. Pat. No. 5,206,806), and ultrasonic sensors (U.S. Pat. Nos. 4,461,178 and 5,456,114). Ultrasonic sensing devices are based on the principles of linear acoustics. These include effects of reflection, scattering, transmission, absorption of probe acoustic energy. The presence of ice coating leads to phase and/or amplitude variation of received signals while the frequencies of the received signals are the same as of emitted probe signals.

None of these previous efforts, taken either alone or in combination teach or suggest all of the elements, nor all of the benefits and utility of the present invention.

OBJECTS AND SUMMARY OF THE INVENTION

It is a principal object of the present invention to provide a method and apparatus for the non-destructive inspection and evaluation of defects in structures and/or ice on structures.

It is another object of the present invention to provide a method for detecting and locating defects in structures, or ice on structures, on the basis of the modulation response of the structures.

It is an additional object of the present invention to provide a method and apparatus for detecting and locating defects in structures, or ice on structures, by observing the modulation of high frequency ultrasonic signal by low frequency vibration.

It is another object of the present invention is to provide a method and apparatus for detecting and locating defects in structures, or ice on structures, which method and apparatus have high sensitivity and which are applicable to highly non-homogenous structures including composites, engine components, etc.

It is even another object of the present invention to provide a method and apparatus for locating a defect in a structure, or ice on a structure, by varying the relative position between a point of application of the low frequency vibration and a receiver.

It is still another object of the present invention to provide a method and apparatus for locating defects in a structure, or ice on a structure, wherein the low frequency signal provides a localized area of increased excitation which increases the side bands of the received signal when positioned near a defect.

It is still another object of the invention to provide a method and apparatus for localization of defects in structure by transmitting and selecting a sequence of short bursts of the high frequency signal modulated by the low frequency vibration.

The modulation acoustic testing method and apparatus of the present invention employs a high frequency probing signal and a low frequency vibration signal. These signals are applied to a structure for testing the integrity of the structure. If there is a defect, the low frequency signal causes modulation of the high frequency probing signal. This modulation manifests itself as side-band components in the spectrum of the received high frequency signal. This indicates a defect in a structure or ice on the structure.

There are three modes of modulation method: a vibro-modulation (VM) method where a harmonic vibration is applied with a shaker; an impact-modulation (IM) method where impact vibration is applied with an instrumented hammer; or a self-modulation (SM) method using modulations with vibration present in the structure due to environment (turbulence, traffic, etc.) and/or working conditions (engine, pumps, motors, water flow, etc.).

The defects may also be quantitatively analyzed if the frequency of the high frequency signal is swept over a defined frequency range and the amplitudes of the side bands are measured, averaged, and normalized. The resulting number indicates the size of the defect.

The location of the defect can also be determined. This is called localization. The invention includes two localization modes of operation.

In the first localization mode, the low frequency signal is moved relative to the probe signal and the probe signal is triggered immediately after the low frequency signal. The low frequency signal creates an area of localized distortion. As the low frequency signal is moved near to a defect, the amplitude of the side bands of the received signal is increased.

In the second localization mode, a sequence of short burst high frequency signals is radiated and a signal-processing algorithm is employed which selects the sequences reflected from various areas of the structure tested. The presence the modulation in the selected sequence will indicate the presence of a defect in the respective area.

The present invention also relates to the nondestructive detection of ice on solid surfaces such as aircraft wings, road pavements, etc. The interface between the ice and structure, for the purpose of this invention, can be considered a defect. When used in this manner, ultrasonic probing signals and low frequency vibration signals are applied to a structure to detect ice. The low frequency vibration signals could be either generated in the structure by VM or IM or already present in the structure by operations involving the structure (SM).

Additionally, it should be pointed out that a bonded composite structure can be tested by the present invention for detection of defects relating to unbonding and also for assessing the quality of the bondings that are in place.

BRIEF DESCRIPTION OF THE DRAWINGS

Other important objects and features of the invention will be apparent from the following Detailed Description of the Invention taken in connection with the accompanying drawings in which:

FIG. 6b shows the spectrum of the samples of FIG. 6a.

DETAILED DESCRIPTION OF THE INVENTION

The present invention relates to a method and apparatus for detecting and locating defects in structures. The invention employs modulation of a high frequency probing signal with a low frequency vibration signal. The invention includes three modes of modulation, namely, a vibro-modulation method, an impact-modulation method and a self-modulation method. Defects may be quantitatively analyzed by sweeping the high frequency signal over a defined frequency range and examining the amplitudes of side bands that are measured, averaged and normalized. The present invention also relates to the localization of defects and includes two localization modes of operation, namely, a first localization mode wherein the low frequency signal is moved about the structure relative to the probe signal, and a second localization mode wherein sequence of short burst high frequency signals are radiated and a signal-processing algorithm is employed to select sequences reflected from various areas of the tested structure to indicate the location of a defect.

Figure 1A:
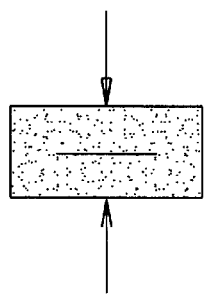
FIGS. 1a and 1b show a defect in contact and out of contact as the stress strain is varied according to the graph of FIG. 1c.
Figure 1B:
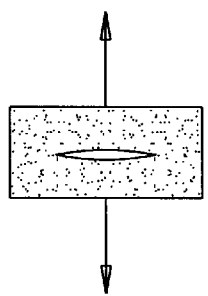
Figure 1C:
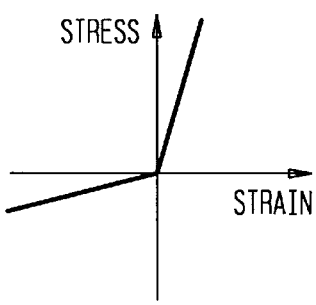

As a brief background, contact-type defects include cracks, unbonds, delaminations, etc. The presence of ice on a structure can be considered, for the purpose of the present invention, a defect. The physical nature of the defect-related modulation is illustrated in FIGS. 1a and 1b, where a defect is modeled as a contact between two flat solid surfaces. If dynamic (acoustic) stress is applied to this defect, there is no contact at all (full opening) during the elongation phase of the stress, and full contact (closure) during the compression phase. The elastic deformation of medium containing such a defect will be different for elongation and compression leading to a piecewise-linear (nonlinear) stress-strain relationship, as shown in FIG. 1c.

Figure 2A:
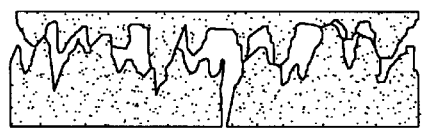
FIG. 2a shows a rough surface defect and its stress strain relationship is shown in the graph of FIG. 2b.
Figure 2B:
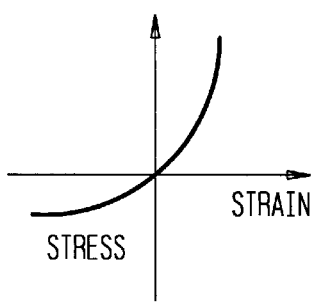

A more realistic model of a defect is a contact between two rough elastic surfaces as shown in FIGS. 2a and 2b. The applied stress will vary the contact area within the defect, leading to a nonlinear elastic deformation.

The stress-strain dependence of a medium containing such contact-type defects will also be nonlinear and can be written in the form of the Taylor's expansion with respect to strain. For simplicity, this relationship can be written for one-dimensional longitudinal deformations:

$$\sigma = E(\epsilon + \beta \epsilon^2 + \gamma \epsilon^3 + \dots), \qquad (1)$$

where $\sigma$ is the stress, $\epsilon$ is the strain, E is the modulus of elasticity, $\beta$, $\gamma$, . . . are the nonlinear parameters, which characterize the nonlinearity of the medium. For the small strains used in acoustic NDT, the cubic and higher terms in this expansion can be neglected and the equation (1) retains only linear and quadratic terms of $\epsilon$. This is the case of so called quadratic nonlinearity. Typical values of the nonlinear parameter $\beta$ as a rule do not exceed 10 for homogeneous media without any defects, so the contribution of the nonlinear quadratic term into the relationship (1) is very small (for small strains) and the media exhibit quasi-linear behavior. The defects may increase the parameter $\beta$ up to two to three orders of magnitude. Even though the value of the nonlinear term may still be small compared with the linear term ($\beta\epsilon \ll 1$), its contribution and, consequently, acoustic manifestations are much more visible.

There are various nonlinear acoustic manifestations of the contact-type nonlinearity. One of them is the modulation of a probe ultrasonic wave by lower frequency vibration. In this case, vibration varies the contact area (or alters defect opening) modulating the phase and the amplitude of the higher frequency probe wave.

Figure 5A:
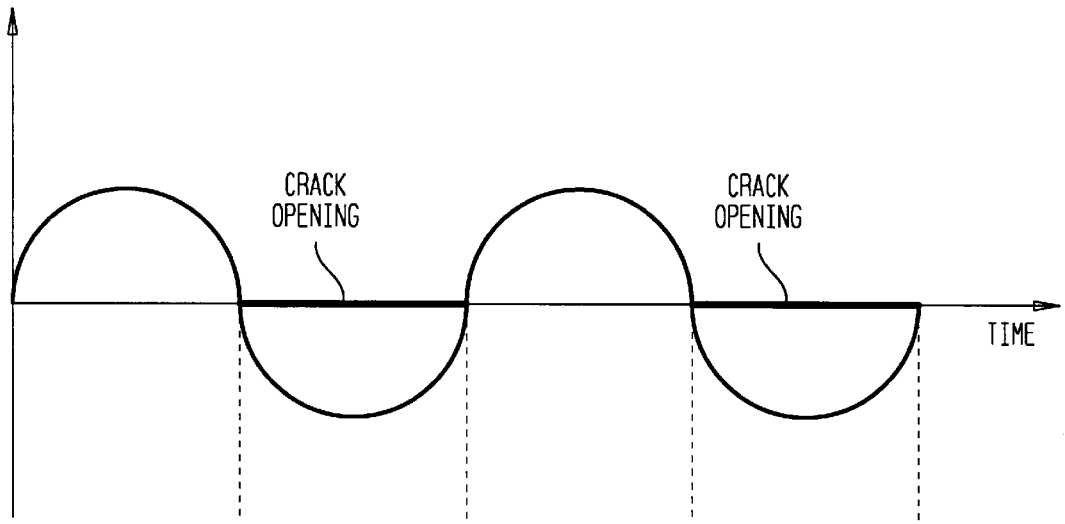
FIGS. 5a and 5b are graphs of the modulation of the high frequency signal by the low frequency vibration. Rarefaction phase of vibration opens a crack reducing intensity of the passing through high frequency signal.
Figure 5B:
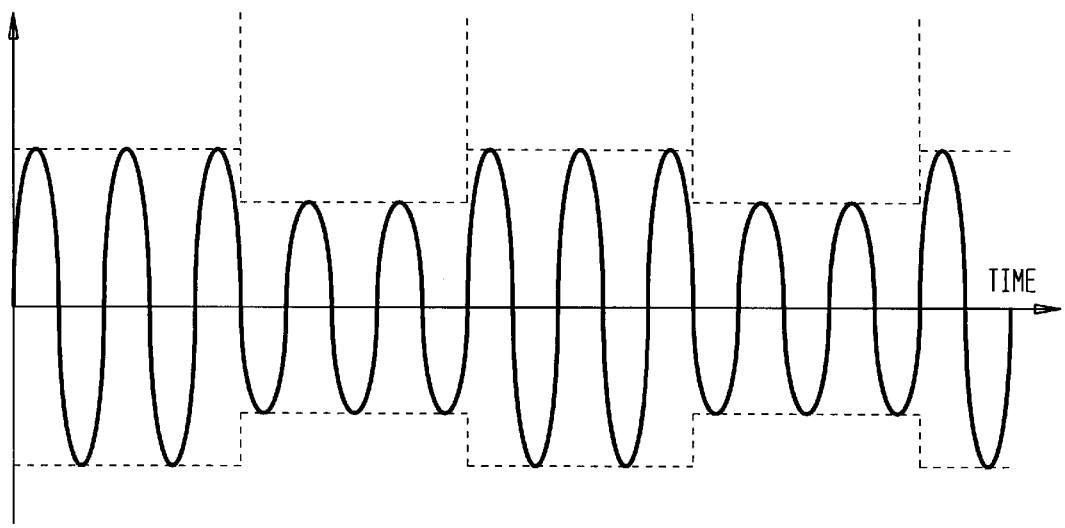

When dynamic low frequency stress (vibration) is applied to the crack, the crack opens in the phase of elongation and closes in the phase of compression, as shown in FIG. 1. If the probe high frequency wave is passing through, its intensity will diminish on the elongation phase of the low frequency stress (crack is opened) as is shown in the FIG. 5, leading to amplitude to modulation of the probing signal by low frequency vibration. In the spectral domain such a modulation manifests itself as sideband components with respect to the carrier ultrasonic signal frequency peak. Obviously, the level of modulation is proportional to the size of the crack, since the larger the crack, the more pronounced the effect of modulation.

Figure 3A:
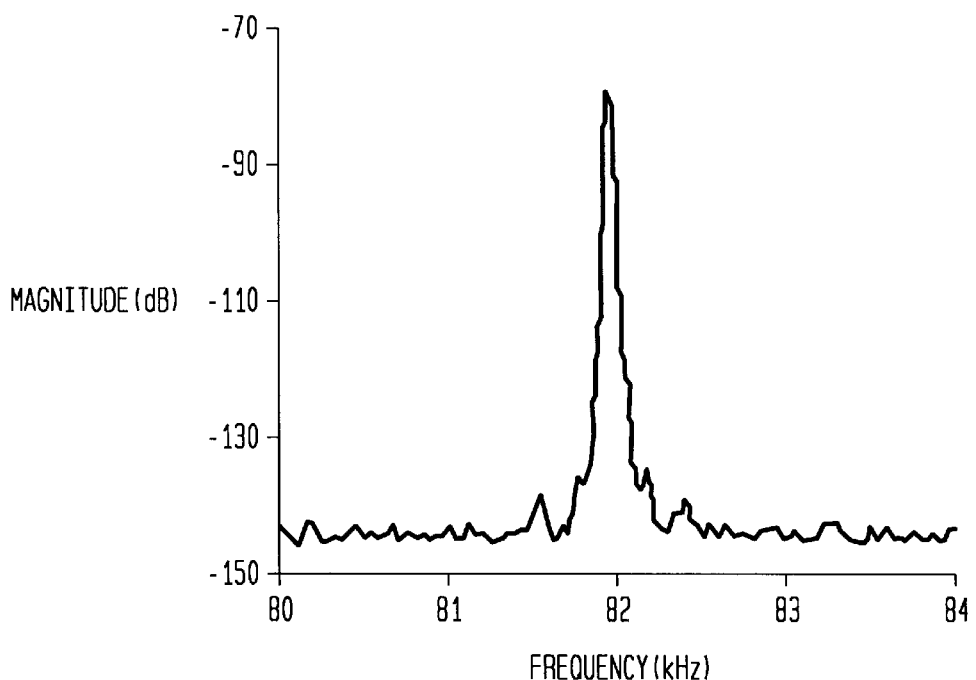
FIGS. 3a and 3b are graphs of the spectra of a probe signal modulated by an impact vibration in a steel pipe with and without defects.
Figure 3B:
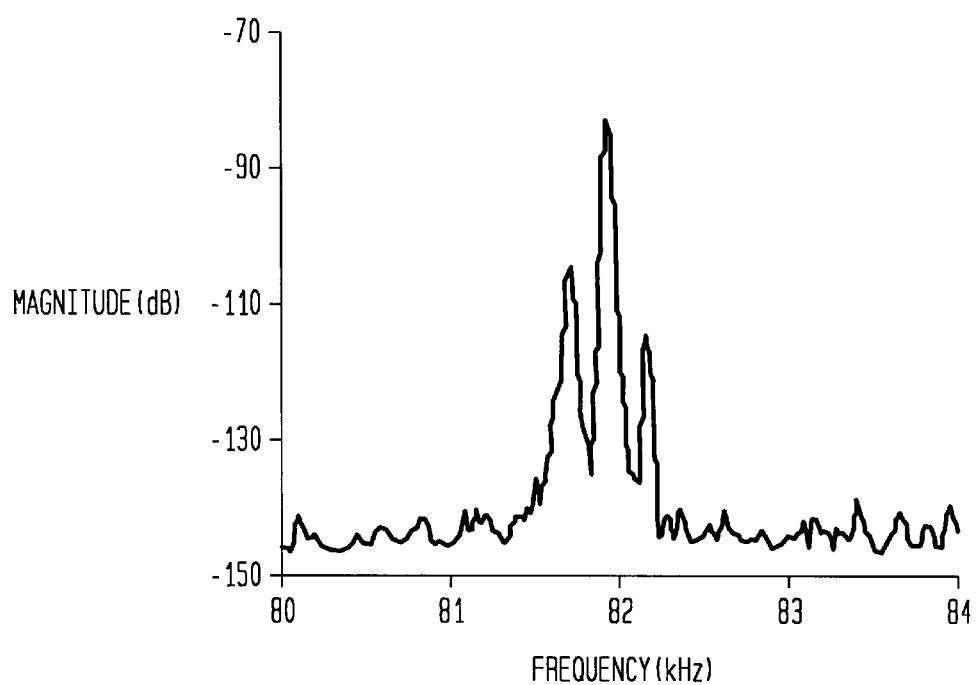

This modulation effect can be observed for various types of defects. FIGS. 3a and 3b show the spectra of a probe signal modulated by an impact vibration observed in a steel pipe with and without defects. This modulation method has high sensitivity and geometric indifference, and can be used for the non-destructive testing of pipes, welded pipes, valves, airplane wings, etc., as well as for structures or equipment which have an intrinsic vibration including operational machinery (pumps, steam, generators, turbines, etc.) water or gas pressure fluctuations, etc.

Figure 4:
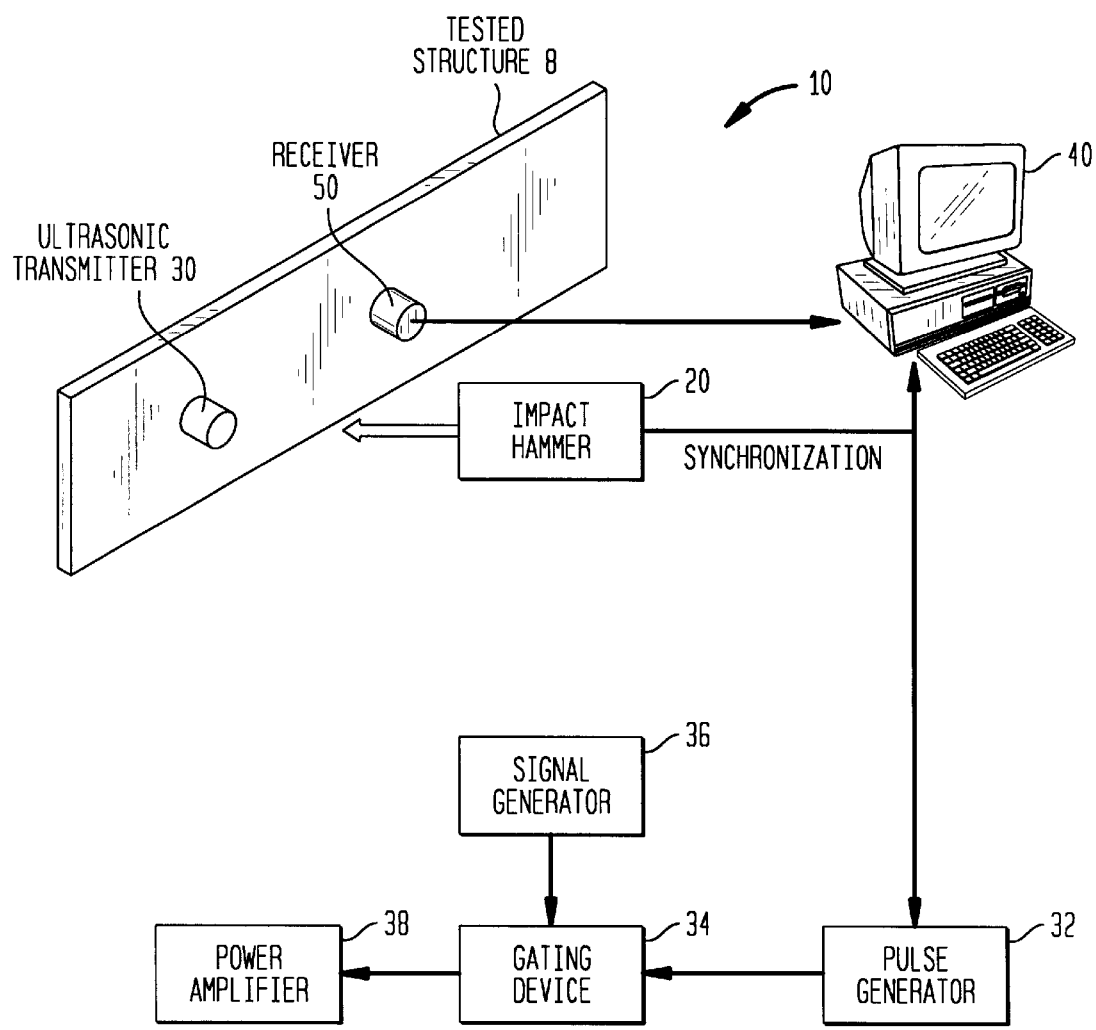
FIG. 4 is a block diagram of the components of the method and apparatus for acoustic detection of defects of the present invention.

Referring to FIG. 4, one representation of the apparatus of the present invention, generally indicated at 10, is depicted. The device includes an impact hammer 20 or other means for creating a low frequency vibration system in the structure 8 to be tested. Alternate means of creating a low frequency vibration signal can be used as is known in the art.

Additionally, a high frequency probe signal is applied to the tested structure 10 by means of an ultrasonic transmitter 30 or other means known in the art. The probing signal is created by a pulse generator 32 which sends a signal to a gating device 34. A signal generator 36 also sends a signal to the gating device which gates the signals and sends its output to power amplifier 38 which delivers the signal to the ultrasonic transmitter 30. The apparatus configuration can, of course, be varied in accordance with what is known in the art.

The hammer 20 includes a sensor which generates a signal for synchronization of system, including the computer means 40 and the pulse generator 32. A receiver 50 is positionable on the tested structure to receive the modulated signal. An array of receivers 50 can be utilized. The receiver 50 picks up and sends the modulated signal to the computer means 40 for analysis.

Due to the presence of defects, the low frequency vibration modulates the high frequency probe signal. This modulation manifests itself as a side band component in the spectra of received signal. Recent examples of the applications of these methods include detection of: unbonding of titanium plates used for airspace applications; cracks in Boeing 767 steel fuse pins; cracks in combustion engine cylinder heads; cracks in a weld in a steel pipe at a nuclear power station; adhesion flaws in bonded composite structures; cracks and corrosion in reinforced concrete; and cracks in rocks. There is strong correlation between presence of contact-type defects such as cracks, debondings, delaminations and measured sideband spectral components. In some experiments the level of the sideband components (in presence of a defect) exceeded the reference signal (without defect) by over 30 dB. These tests demonstrate capability of the modulation methods to detect flaws in highly non-homogeneous structures where conventional acoustic methods are not applicable. Among such structures are composite materials, airframes and engine components, civil structures, etc.

The present invention can be used in another mode to determine the location of the defect. In the first localization mode, the low frequency signal is moved relative to the probe signal and the probe signal is triggered immediately after the low frequency signal. The low frequency signal creates an area of localized distortion. As the low frequency signal is moved near to a defect, the amplitude of the side bands of the received signal is increased.

In the second localization mode, a sequence of short burst high frequency signals is radiated and a signal-processing algorithm is employed which selects the sequences reflected from various areas of the structure tested. The presence of the modulation in the selected sequence will indicate the presence of a defect in the respective area.

More particularly, the first localization mode involves varying the relative distance between the probing signal, the low frequency signal and the receiver, such as by moving the low frequency signal around the tested structure and analyzing the signal. Upon an impact by an impact hammer, a localized area of increased excitation around the area of impact is formed, which thereafter becomes a waveform. It is the waveform that is used to modulate the high frequency probing signal in the testing mode. However, the localized impact distortion is relied upon in the localization mode. The computer acquires a probe signal that has been delayed from impact to exclude the vibration caused by the localized stress of the impact hammer. The probe signal is acquired immediately after impact to correspond to the short lived localized vibration of the impact hammer. By utilizing the localized vibration, the amplitude of the sidebands of the received signals is increased when the impact hammer is located near a defect. An impact produced vibration field can be represented by two parts: near field stress (localized in the vicinity of the impact) and propagating wave stress. As a rule, near field stress is much greater than propagating wave stress. The propagating wave field may cover the entire structure; this leads to modulation of the ultrasonic probing signal in the presence of a defect. This modulation serves as an indication of the defect. With this, the closer the impact to the defect, the greater the near field stresses applied to it, leading to a higher modulation level. Therefore, impacting at different locations and correlating the impact location and level of the modulation allows for locating defects.

In the second localization mode, localization of a defect is achieved by varying the parameters of applied ultrasonic and vibration inputs. Higher frequency ultrasonic waves may irradiate a smaller part of the tested structure, so the inspected area can be reduced accordingly. In addition, the location of a defect can be determined by varying the location of the applied impact. A new algorithm using periodic burst ultrasonic signals has been developed. Sequences of the burst ultrasonic signals are transmitted. Each burst has a carrier frequency fc. The duration between the burst is determined by the repetition frequency Fr.

Figure 6A:
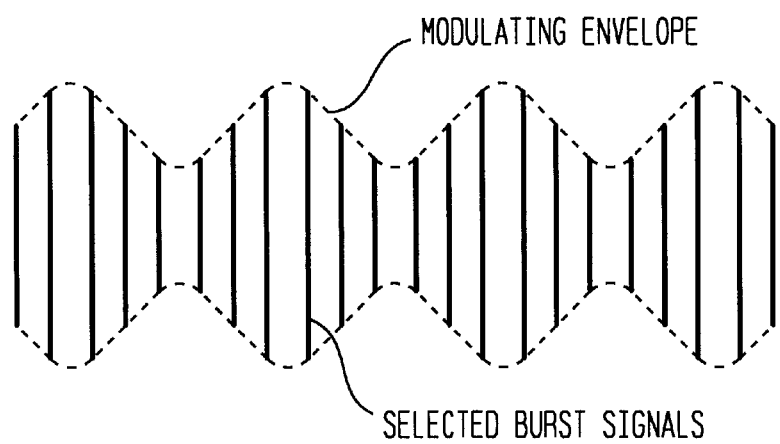
FIG. 6a illustrates selected series of modulated ultrasonic burst samples.
Figure 6B:
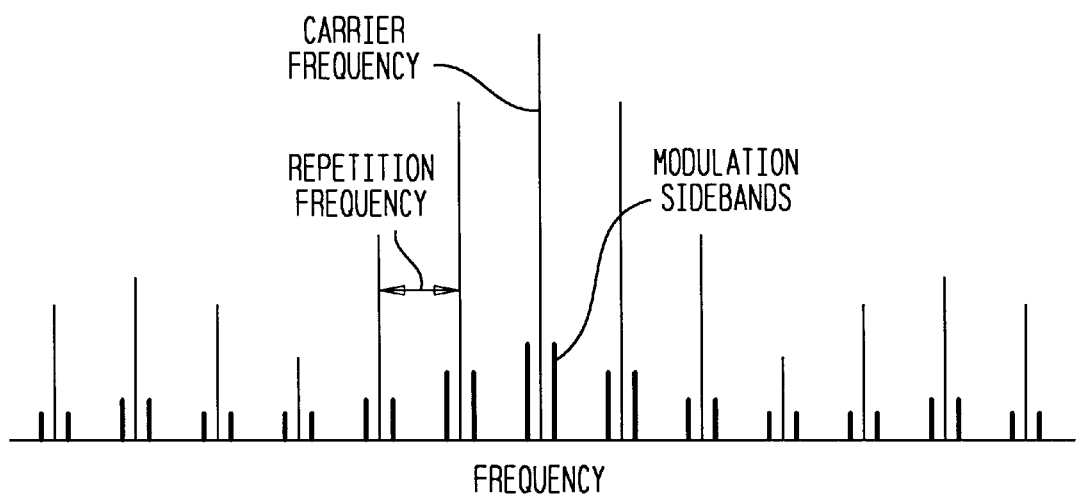

The algorithm selects and processes only those bursts which travel/reflect within/from the area of interest. The duration of each burst is sufficiently short to be resolved from the signal reflected from the other parts of the structure. The repetition frequency, Fr, is chosen to satisfy the following condition: Fr>2Fv, where Fv is the frequency of the modulation vibration. This is equivalent to the Nyquist frequency condition, since the selected pulses will be used to "sample" the modulation envelope, as illustrated in FIGS. 6a and 6b.

Figure 7:
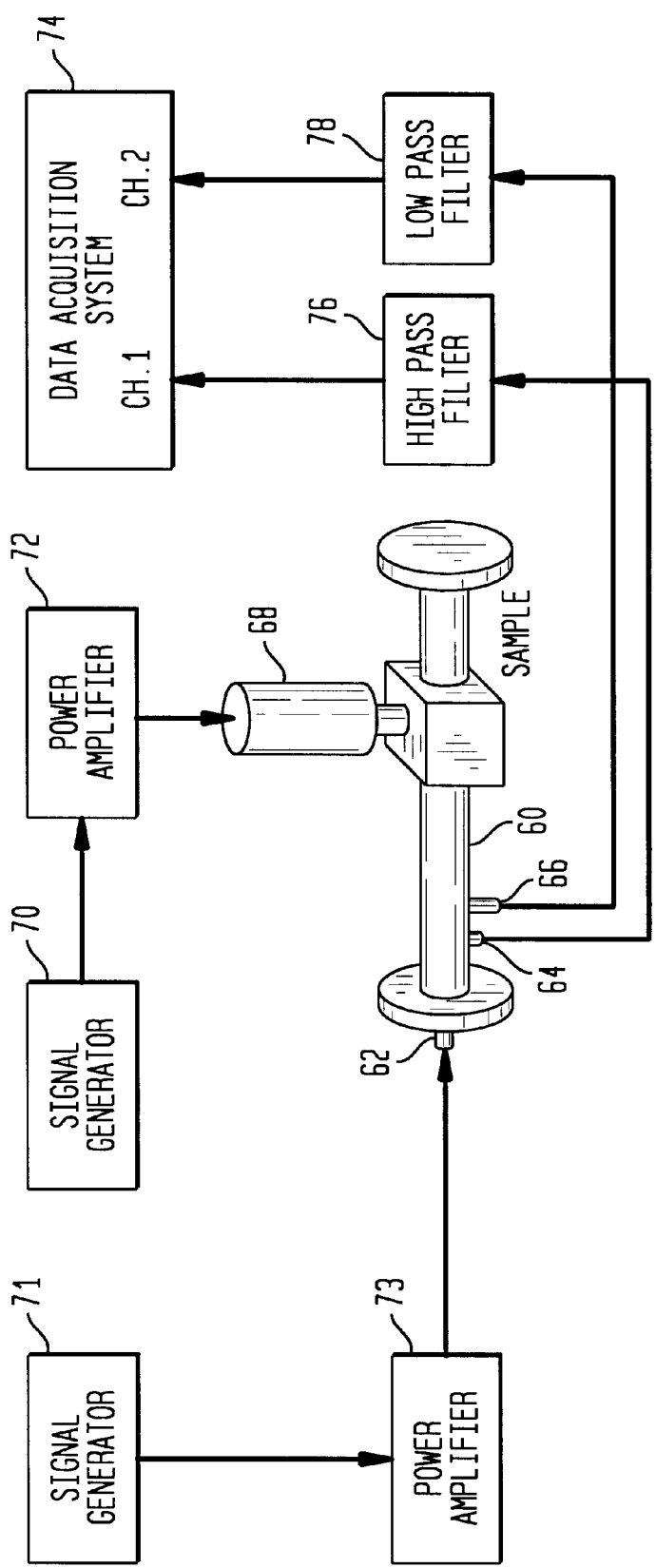
FIG. 7 is a block diagram of apparatus for detecting defects in a steel pipe.

The algorithm has been tested using a steel pipe 60 with welded flanges as shown in FIG. 7. One of the flanges has a defect (a crack). The opposite flange is free of defects. The pipe 60 has an ultrasonic transmitter 62 attached to one end thereof. An ultrasonic receiver 64 and an accelerometer 66 is coupled to the pipe. A shaker 68 is also coupled to the pipe. The shaker 68 is driven by signal generator 70 and a power amplifier 72. The ultrasonic transmitter 62 is driven by signal generator 71 and power amplifier 73. In practicing the method of this invention, the ultrasonic transmitter 62 generates the high frequency signal and the shaker 68 provides the low frequency signal. The receiver 64 is coupled to data acquisition system 74 via a high pass filter 76. The accelerometer 66 is coupled to the data acquisition system 74 via a low pass filter 78.

Figure 8A:
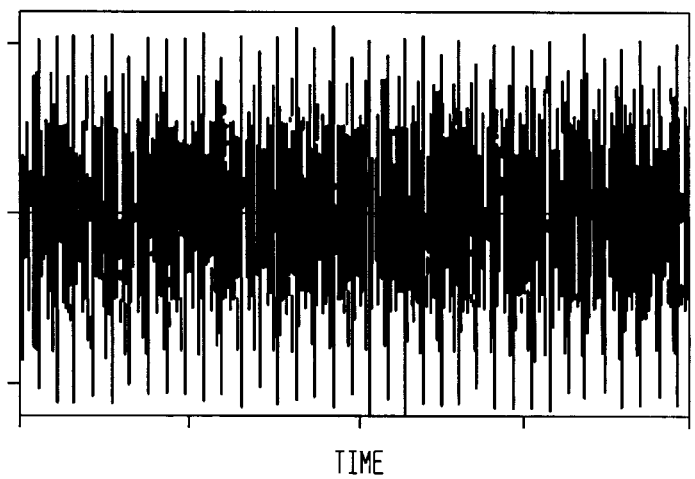
FIGS. 8a–8c illustrate transmitted and received signals in the apparatus of FIG. 7.
Figure 8B:
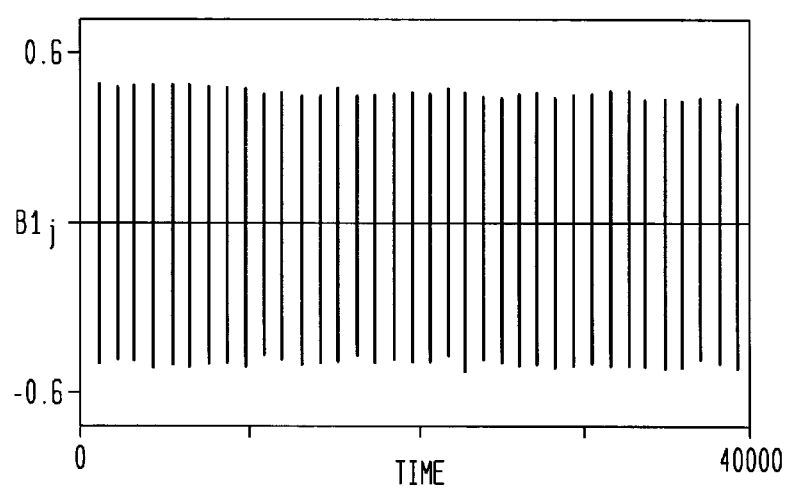
Figure 8C:
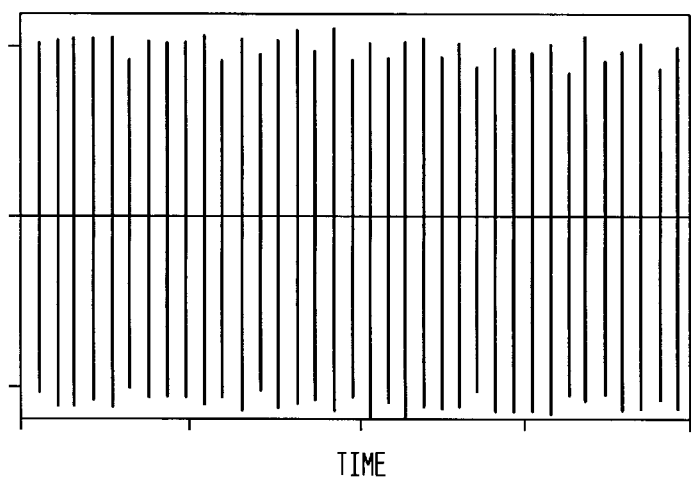
Figure 9A:
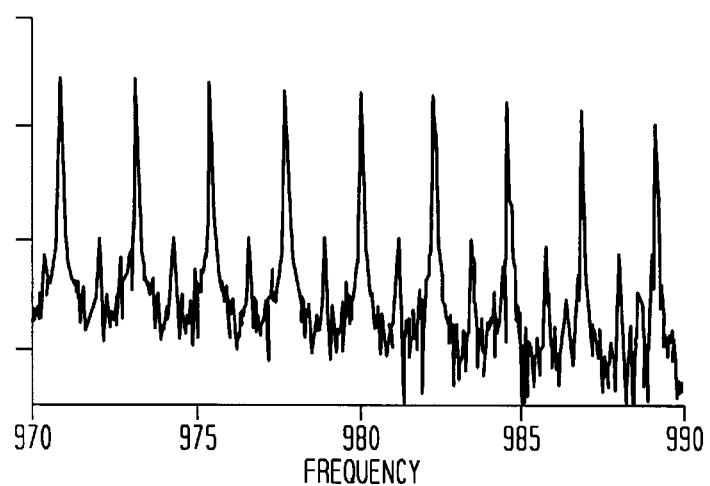
FIGS. 9a–9c illustrate the spectra of the signals of FIGS. 8a–8c, respectively.
Figure 9B:
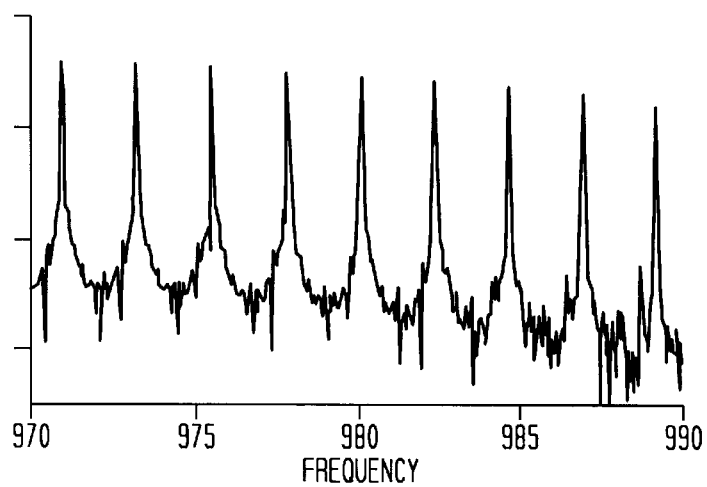
Figure 9C:
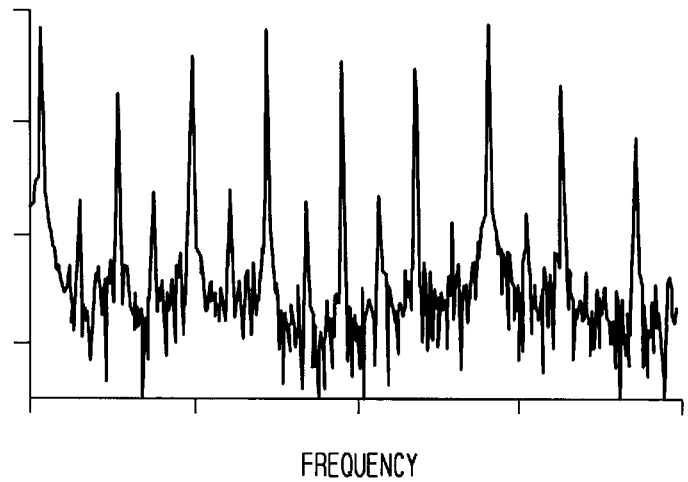

FIG. 8a shows a series of 50 μs bursts with the carrier frequency near 1 MHz received from the sample. The frequency of repetition is 1600 Hz. The frequency of applied vibration is 494 Hz. As shown in FIG. 8a, the received waveform has signals reflected from both flanges. FIG. 8b and FIG. 8c shown the selected burst reflected from the defective and the defect-free flanges. FIG. 9a shows the spectra of the entire waveform. FIGS. 9b and 9c show the spectra of corresponding selected sequences of the bursts reflected from the flange containing the defect. These spectra demonstrate the presence of the modulation in the sequence of the bursts reflected from the flange containing a defect (FIG. 9c). No modulation of the sequence of bursts reflected from the defect-free flange is shown.

The method of the present invention also enables defects to be quantitatively analyzed. The frequency of the high frequency signal is swept over a defined frequency range and the amplitudes of the side bands are measured, averaged, and normalized in accordance with the following equation: M=Am/ApAv where Am is the amplitude of the side band signal, AP is the in amplitude of the high frequency signal and Av. is the amplitude of the low frequency signal. The resulting number, M, indicates the size of the defect. The number of steps in the frequency range selected is typically 10–20. The range of frequency over which the measurements are taken is typically 10–30 kHz.

The present invention also relates to the nondestructive detection of ice on solid surfaces such as aircraft wings, road pavements, etc. The interface between the ice and the structure, for the purposes of this invention, can be considered a defect. When used in this manner, ultrasonic probing signals and low frequency vibration signals are applied to a structure to detect ice. The low frequency vibration signals could be either generated in the structure or already present in the structure by operations involving the structure. These operations may include vibrations from an engine or low frequency signals due to turbulence. The vibrations may also be present in a structure due to the environment as by traffic or the wind.

In a structure without ice cover, the ultrasonic probe signal and the low frequency vibration signal propagate independently without any interaction. If the structure is covered with ice, there is significant interaction between the ultrasonic probe signal and the low frequency vibration. The ultrasonic probe signal is modulated by the low frequency vibration signal. In the frequency domain, the modulation appears as sideband spectral components with respect to the frequency of the ultrasonic probe signal. These sideband spectral components are considered as new signals associated with the presence of ice, so that the ice can be more easily detected when such signals are observed.

Ice may be detected in aircraft, road pavement, bridges, etc. using this method. Ultrasonic and vibration signals are applied to and received from the inspected structure in the area of interest. The method may operate to detect the presence or absence of ice. The method may also operate in a localized manner to locate the iced area using burst signals and the described above signal-processing algorithm.

The modulation method of the present invention has a number of advantages over acoustic techniques used in the prior art. In the prior art linear techniques, variation of linear acoustic parameters, which indicate the presence of ice, may depend on other factors such as temperature changes or structural load. These other factors cause a similar or greater effect on the measured parameters than the presence of ice. The modulation method of the present invention is not affected by these factors, as they do not cause modulation of the probe signal.

Figure 10:
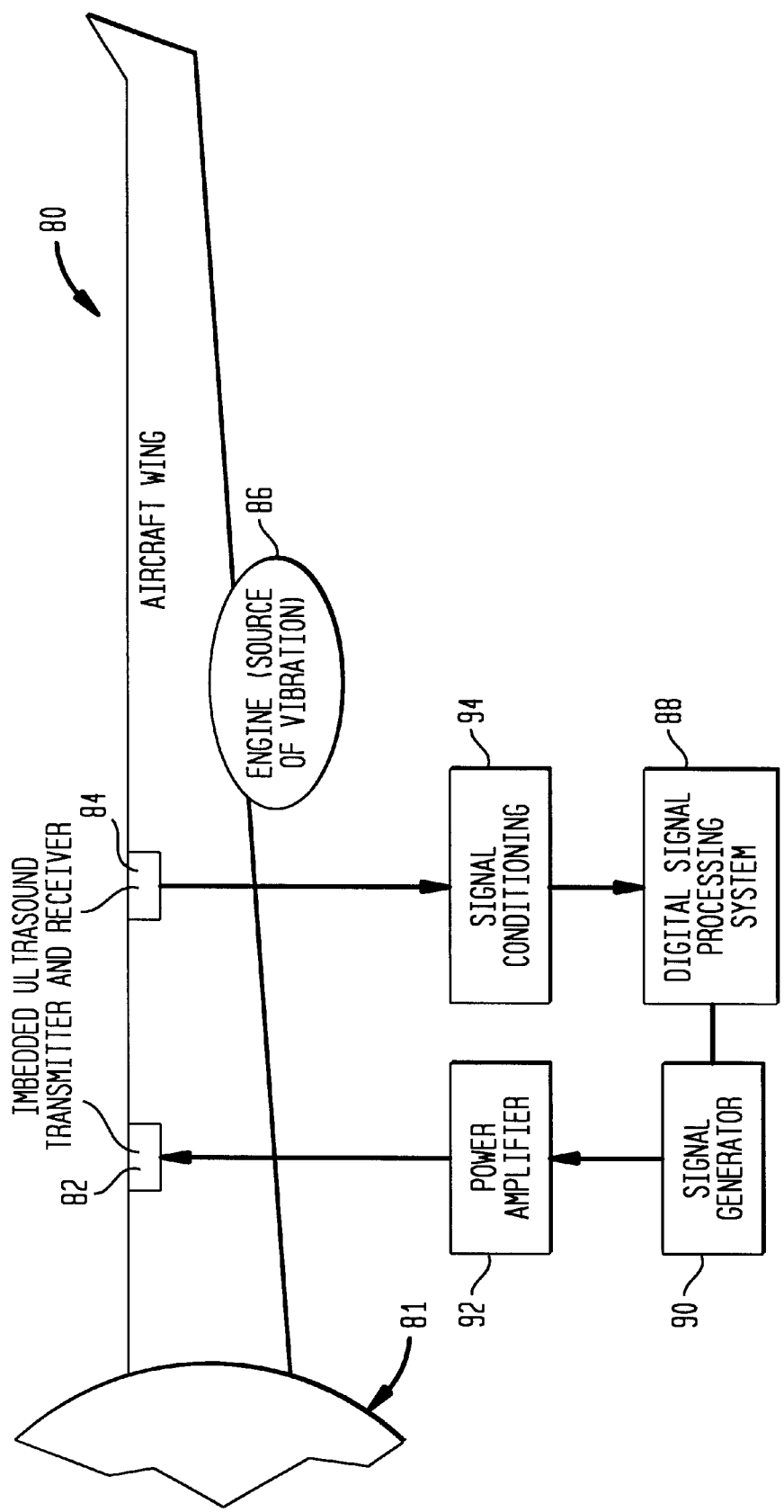
FIG. 10 is a block diagram of apparatus to detect ice on an air plane wing.

The method of this aspect of the present invention can be implemented on an aircraft wing is shown in FIG. 10. Aircraft wing 80 is connected to an aircraft body 81. The wing 80 has ultrasonic transmitter 82 and an ultrasonic receiver 84 embedded therein. A source of low frequency vibrations such as aircraft engine 86 is also attached to the wing 80. A digital signal processing system 88 is connected to signal generator 90, which is in turn connected to a power amplifier 92 for generating the transmitted signal. The processing system 88 is also connected to receiver 84 via a signal-conditioning device 94.

Figure 11A:
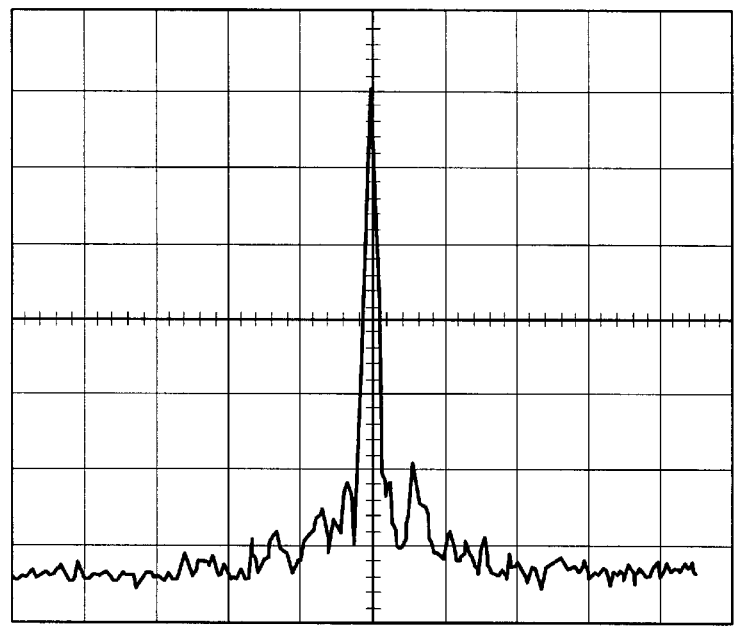
FIGS. 11a–11b are spectral diagrams of signals from an aluminum plate with and without ice.
Figure 11B:
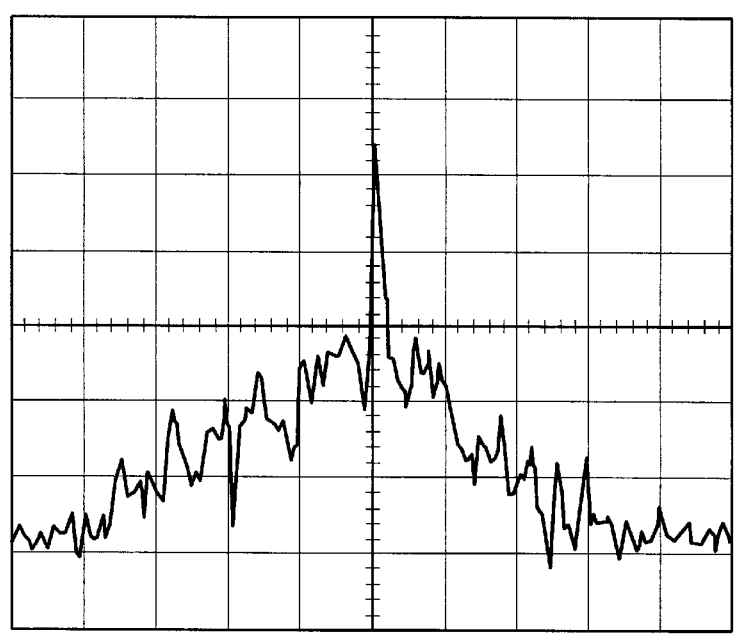

FIGS. 11a and 11b show the spectra of received signals from an aluminum plate that was placed within a freezer. Two identical piezoceramic disks (ultrasonic transmitter and receiver) were glued to the plate. The vibration signal was generated with a hammer. The modulation was monitored before and after spraying water on the plate. A dramatic increase in modulation occurred even with only a small area of ice (10%). The spectrum of the received signal from the plate without ice is shown in FIG. 11b. The spectrum of the received signal from the plate with 10% of its area covered with ice is shown in FIG. 11(b). The presence of ice increases the amplitude of the side-band components of the received signal up to 20 dB.

Having thus described the invention in detail, it is to be understood that the foregoing description is not intended to limit the spirit and scope thereof. What is desired to be protected by Letters Patent is set forth in the appended claims.

What is claimed is:

1. An apparatus for detecting the presence and characteristics of a defect in or ice on a structure comprising:
    means for creating and delivering a low frequency signal to the structure;
    means for creating and delivering a high frequency probe signal to the structure; and
    receiver means for receiving a modulated signal from the structure caused by the low frequency signal modulating the high frequency signal in response to a defect in or ice on the structure, the modulated signal indicating the presence of a defect in or ice on the structure.

2. The apparatus of claim 1 further comprising means for moving the low frequency signal relative to the high frequency probe signal and receiver means; and means for triggering the probe signal after the low frequency signal to locate a defect in the structure.

3. A method of detecting the presence and characteristics of a defect in or ice on a structure comprising the steps of:
    applying a low frequency signal to the tested structure;
    applying a high frequency probe signal to the tested structure;

modulating the high frequency signal by the low frequency signal in response to the presence of a defect in the structure; and receiving a modulated signal through a receiver means applied to the tested structure.

4. The method of claim 3 further comprising locating the defect in the structure by triggering the probe signal to occur immediately after the low frequency signal is applied to the tested structure; moving a point of delivery of the low frequency signal about the tested structure; and monitoring the amplitude of the modulated signal for increased modulation.

5. A method for detecting the presence and characteristics of a defect in or ice on a structure comprising the steps of:

propagating an ultrasonic probe signal in the structure;

propagating a low frequency vibration signal in the structure;

detecting said ultrasonic probe signal and analyzing said detected ultrasonic probe signal for interaction between said ultrasonic probe signal and said low frequency vibration signal caused by a defect in or ice on the structure, said interaction being indicative of a defect in or ice on the structure.

6. The method of claim 5 wherein said interaction is a modulation of said ultrasonic probe signal by said low frequency vibration signal.

7. The method of claim 6 wherein said modulation appears as sideband spectral components with respect to a frequency of said ultrasonic probe signal.

8. The method of claim 7 wherein said sideband spectral components are associated with the presence of a defect in or ice on the structure.

9. The method of claim 6 wherein said low frequency signal exists in said structure because of the operation or the environment of the structure.

10. A method of determining the location and characteristics of defects in or ice on a structure comprising the steps of:

propagating sequences of an ultrasonic probe signal in a structure;

said ultrasonic probe signal having a first frequency;

said sequences being propagated at a second repetition frequency;

propagating a low frequency vibration signal in said structure the low frequency vibration signal modulating the ultrasonic probe signal in response to a defect in or ice on the structure;

detecting said propagated sequences of the probe signal, and selecting and processing only propagated sequences which are indicative of an area of said structure having a defect or ice.

11. The method of claim 10 wherein said second repetition frequency is sufficiently short to be resolved from the ultrasonic probe signal reflected from the other areas of said structure.

12. The method of claim 11 wherein said second repetition frequency is greater than twice the frequency of said low frequency vibration signal.

13. An apparatus for non-destructive testing of a structure comprising:

means for transmitting an ultrasonic signal into said structure;

means connected to said structure for receiving said ultrasonic signal;

means connected to said structure for generating a low frequency signal in said structure; and control means connected to said transmitting means and to said low frequency generating means for transmitting said ultrasonic signal into said structure at a repetition frequency which is greater than twice the frequency of said low frequency signal;

wherein, the low frequency signal modulates the ultrasonic signal in response to a defect in the structure.

14. The apparatus of claim 13 wherein said low frequency signal is generated from the operation or the environment of said structure.

15. An apparatus for determining the location and characteristics of defects in ice on a structure comprising:

means for generating a low frequency signal in a structure;

means for generating a high frequency signal in the structure;

means for receiving a modulated signal from the structure caused by said low frequency signal modulating said high frequency signal in response to a defect in or ice on the structure; and means for analyzing side bands in said received signal for analyzing a defect or ice.

16. The apparatus of claim 15 wherein said means for generating a low frequency signal includes a shaker.

17. The apparatus of claim 15 wherein said means for generating a low frequency signal includes an instrumented hammer.

18. The apparatus of claim 15 wherein said means for generating a low frequency signal includes vibrations present in the structure due to environment and/or working conditions.

19. An apparatus for quantitatively analyzing defects in a structure comprising:

means for generating a high frequency signal in a structure;

means connected to said high frequency signal generating means for varying the frequency of said high frequency signal over a predetermined frequency range;

means for generating a low frequency signal in said structure;

means for receiving frequency modulated signals from said structure caused by the low frequency signal modulating the high frequency signal in response to a defect in the structure, said received modulated signals being indicative of a defect in said structure; and means connected to said receiving means for measuring, averaging and normalizing the amplitudes of side bands in said received modulated signals to generate an indication of the size of a defect in the structure.

20. The apparatus of claim 15 further comprising:

means for moving location of said low frequency generating means on said structure relative to the location of said means for generating said high frequency signal; and control means for triggering said high frequency signal after said low frequency signal is triggered, whereby the amplitude of said side bands is increased as the location of said low frequency signal generating means is moved towards a defect.

21. An apparatus for locating defects in structures comprising:

means for generating a low frequency signal in a structure;

means for generating sequences of a short burst high frequency signal in the structure;

means for receiving a signal from the structure, said signal being a modulated combination of said low frequency signal and said high frequency signal;

means for analyzing selected sequences of said received signal from areas of the structure;

whereby a presence of modulation in a selected sequence indicates the presence of a defect in an area of the structure.

22. The apparatus of claim 1 wherein the means for delivering a signal comprises an ultrasonic transmitter and the means for receiving a signal comprises an ultrasonic receiver.

23. The apparatus of claim 22, wherein the structure comprises an aircraft wing and the transmitter and receiver are embedded in the wing.

24. The apparatus of claim 22 wherein the transmitter and receiver comprise piezoceramic material.

25. The method of claim 4 wherein modulation of the modulated signal appears as side-band components in the spectrum of the high frequency signal, and the step of monitoring the amplitude of the modulated signal comprises monitoring the amplitude of the side-band components in the spectrum of the high frequency signal.

26. The method of claim 3 wherein the low frequency signal comprises harmonic vibration.

27. The method of claim 26 wherein the harmonic vibration is applied by a shaker.

28. The method of claim 3 wherein the low frequency signal comprises impact modulation.

29. The method of claim 28 wherein the impact modulation is applied with an instrumented hammer.

30. The method of claim 3 wherein the low frequency signal comprises self-modulation.

31. The method of claim 30 wherein the self-modulation is applied by the environment.

32. The method of claim 30 wherein the self-modulation is applied by working conditions.

33. A method of analyzing defects in a structure comprising:

generating a high frequency signal in a structure;

sweeping the frequency of the high frequency signal over a frequency range;

generating a low frequency signal in the structure;

receiving modulated signals caused by the low frequency signal modulating the high frequency signal in response to a defect in the structure; and analyzing side bands of the modulated signals to analyze the defect.

34. The method of claim 33 wherein the step of analyzing the side bands of the modulated signal comprises measuring, averaging, and normalizing amplitudes of the side bands.

35. The method of claim 34 wherein the size of the defect is derived by dividing the amplitude of the side bands by the product of the amplitude of the high frequency signal and the amplitude of the low frequency signal.

36. The method of claim 33 wherein the frequency range has 10 to 20 steps.

37. The method of claim 33 wherein the frequency range comprises 10–30 kHz.

38. A method for locating defects in a structure comprising:

generating a low frequency signal in a structure;

generating sequences of a short burst high frequency signal in the structure;

receiving a modulated signal from the structure caused by the low frequency signal modulating the high frequency signal in response to a defect in the structure;

analyzing modulation of sequences of the received signal from areas of the structure to locate a defect in the structure.

39. The apparatus of claim 21 wherein the means for receiving a signal from the structure comprises an array of receivers.

* * * * *